United States Patent [19]

Boudreault et al.

[11] Patent Number: 5,186,714
[45] Date of Patent: Feb. 16, 1993

[54] MULTIFUNCTIONAL SURGICAL INSTRUMENT

[75] Inventors: Yvon Boudreault; Steven Boudreault, both of Castroville, Calif.; Fernand Jalbert, Sherbrooke, Canada

[73] Assignee: Yab Revo-Tech Inc., Notre-Dame-du-Bon-Conseil, Canada

[21] Appl. No.: 884,768

[22] Filed: May 18, 1992

[51] Int. Cl.$^5$ .................. A61M 1/00; A61B 17/39
[52] U.S. Cl. ................................ 604/21; 604/33; 604/35; 606/15; 606/49
[58] Field of Search .......... 604/21, 30, 32, 33, 604/35; 606/7, 15, 16, 41, 45, 49

[56] References Cited

U.S. PATENT DOCUMENTS

| | | | |
|---|---|---|---|
| 2,545,865 | 3/1951 | Wallace | 606/49 |
| 2,812,765 | 11/1957 | Tofflemire | 604/32 |
| 3,195,536 | 7/1965 | Hovnanian et al. | 128/398 |
| 3,825,004 | 7/1974 | Durden, III | 606/49 |
| 4,451,257 | 5/1984 | Atchley | 604/33 |
| 4,526,573 | 7/1985 | Lester et al. | 604/33 |
| 4,708,717 | 11/1987 | Deane et al. | 604/35 |
| 4,776,840 | 10/1988 | Freitas et al. | 604/35 |
| 4,964,849 | 10/1990 | Robicsek | 604/35 |
| 5,045,055 | 9/1991 | Gonser et al. | 604/33 |
| 5,095,889 | 3/1992 | Weissmüller et al. | 606/16 |

FOREIGN PATENT DOCUMENTS

| | | | |
|---|---|---|---|
| 2037139 | 4/1991 | Canada . | |
| 2042456 | 5/1991 | Canada . | |
| 1293648 | 12/1991 | Canada . | |
| 327410 | 8/1989 | European Pat. Off. . | |
| 463363 | 1/1992 | European Pat. Off. . | |
| 1223895 | 4/1986 | U.S.S.R. | 606/49 |
| 2044104 | 10/1980 | United Kingdom | 606/15 |

*Primary Examiner*—Stephen C. Pellegrino
*Assistant Examiner*—Ralph A. Lewis
*Attorney, Agent, or Firm*—Robic

[57] ABSTRACT

A multifunctional surgical instrument for use in laparoscopic surgery, including a rigid hollow tube, or trocar, mounted on a pistol-grip shaped holder in which a cartridge may be removably mounted, incorporating valves and tubes for connection to a source of vacuum and a source of flushing liquid. The instrument is very simple yet efficient in structure, very handy and easy to use, and designed to allow fast and easy interchange of a tube by another tube incorporating or not electrodes or laser fibers. It can be used through a cannula, not only for irrigation or suction of physiological matter but also for suction of gas or vapors, electrocautery, laparoscopy or laser surgery.

13 Claims, 3 Drawing Sheets

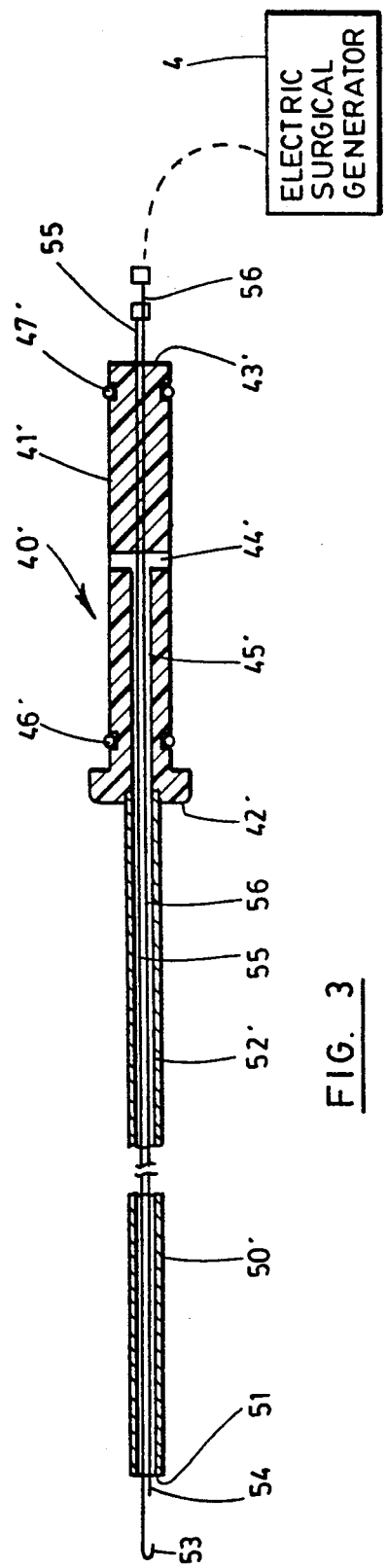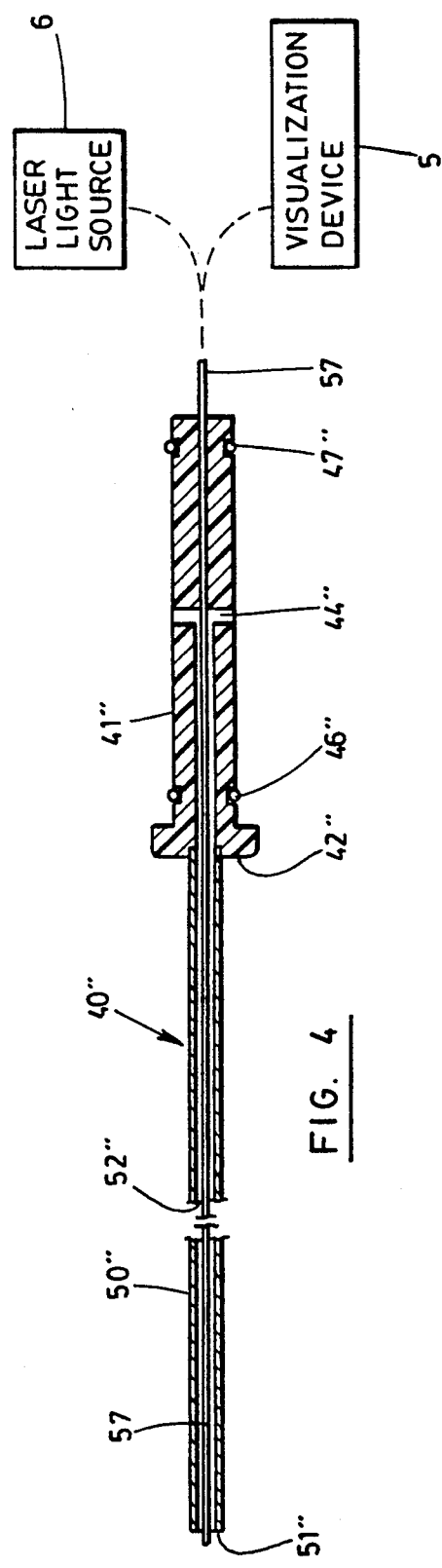

MULTIFUNCTIONAL SURGICAL INSTRUMENT

BACKGROUND OF THE INVENTION a) Field of the Invention

The present invention is concerned with a multifunctional surgical instrument for use in carrying out laparoscopic surgery.

b) Brief Description of the Prior Art

Laparoscopic surgery is a relatively new operating technique that has been developed to carry out percutaneous surgery and more especially cholecystectomy (gallbladder removal) also it could be used in gynecology, meurosurgery and urology.

This technique is much less invasive than a conventional surgery and thus may be carried out using only sedimentation and a local anaesthetic. It involves puncturing the abdominal wall and inducing a pneumoperitoneum to distend the abdomen. A cannula of about 1 cm in diameter is inserted into the puncture and used as a "guiding member" through which one or more surgical instruments may be inserted and guided with great accuracy towards, the body part requiring surgery. Such instruments may include an endoscope (laparoscope), a biopsy needle, a clip applier, microscissors or forceps, a fiber-optic rod connected to a laser source for hemostatic cutting or coagulation, a set of electrodes connected to a generator for electrocautery, etc. . . . If desired, one or more smaller cannulas may be inserted into the 1 cm cannula to work with two or more instruments.

Following the surgery, the puncture may be closed in a very simple manner, using a sterile adhesive strip to do so. This permits to reduce to a minimum extent the patient's stay at the hospital and the period for his or her recovery and resumption of normal activity. This also permits to reduce the post-operation scar.

During surgery, it is often required to irrigate with a flushing liquid, i.e. a saline, or to suction the internal body cavity which may be, for example, the liver bed region or the gallbladder, without having to stop the surgical step that is being carried out. It is also required to evacuate stones or blood clots from the cavity.

To do so, surgical instruments have been devised, which are in the form of a rigid hollow tube also called "trocar", which is connectable to a source of vacuum and a source of flushing liquid. A set of valves known as "trumpet valves" are rigidly mounted at the rear end of the tube and used to sequentially connect the same to both of these sources, respectively, for suction of physiological matter or irrigation purpose.

Recently, it has been suggested to incorporate a pair of bipolar electrodes fed by electrically insulated wires connectable to an electrosurgical generator at the front end of a suction and irrigation tube of the above mentioned type, to make it also useful for coagulating and cauterizing as need may be, thereby increasing the versatility of the instrument while simultaneously reducing the number of instruments to be inserted at the very same type in the cannula (see Canadian laid-open patent application No. 2,037,139 published on Oct. 31, 1991 to EVEREST MEDICAL CORP.) It has also been suggested to mount such a suction and irrigation tube in a detachable manner onto a pistol-grip shaped holder incorporating the required set of valves so that these valves be actuable with a finger like a pistol trigger, so as to facilitate manipulation of the instrument in use (see Canadian laid-open patent application No. 2,042,456 published on Nov. 26, 1991 to Edward H. PHILLIPS). This pistol-shaped instrument which may incorporate or not a set of electrodes for electrocautery or a laser optic fiber bundle for laser surgery techniques, is much more handy than those used so far. However, the valve assembly in the holder is not readily accessible and easy to change whenever required. Moreover, the tube is attached to the holder by means of screws, thereby making an interchange rather difficult to carry out during an operation.

OBJECTS AND SUMMARY OF THE INVENTION

A first object of the invention is to provide a surgical instrument of the above mentioned type, for use in carrying out laparoscopic surgery, including a rigid hollow tube mounted on a pistol-grip shaped holder incorporating a set of valves, which is very simple yet efficient in structure which is very handy and easy to use, and which is so designed as to allow fast an easy interchange of the tube by another tube incorporating or not electrodes or laser bundles whenever desired.

Another object of the invention is to provide a surgical instrument of the above mentioned type, wherein not only the tube but the set of valves and associated tubings are easily interchangeable, the valves and tubings forming together a kind of disposable "cartridge" that can easily be inserted into the holder and removed therefrom.

A further object of the invention is to provide a surgical instrument of the above mentioned type, which is multifunctional and versatile and can be used not only for irrigation with a flushing-liquid or suction of physiological matter through a cannula, but also for suction of gas or vapors, electrocautery, laparoscopy or laser surgery through the same cannula.

In accordance with the invention as broadly claimed hereinafter these objects are achieved with a multi-functional surgical instrument for use in carrying ou laparoscopic surgery, comprising, in combination:

A) a pistol-shaped holder including a handle shaped as a pistol-grip to facilitate holding and manipulation of the instrument;

B) a suction and irrigation cartridge connectable to a source of vacuum and a source of flushing liquid including a set of valves this cartridge being preferably disposable, and C) an interchangeable surgical tool including a trocar, which is detachably connectable to the holder and easily interchangeable with another similar one.

More particularly, the pistol-shaped holder A) used in the instrument according to the invention includes:

(i) a handle shaped as a pistol-grip; and
(ii) a hollow cylinder shaped, positioned and oriented as a pistol-barrel on top of the handle, this cylinder having an open front end and a rear end.

This pistol-shaped holder (A) is preferably made of two symmetrical parts that are detachably connected and each define half of the handle (i) and half of the cylinder (ii).

The suction and irrigation cartridge (B) used in the instrument according to the invention is mounted within the handle and connectable to a source of vacuum and a suorce of flushing liquid. It includes:

(i) a tree way valve mounted inside the handle, the valve including:
  first, second and third fluid ports and first and second spring-biased valve plugs operable by first and second push-buttons respectively, the first valve plug being devised to place in fluid communication the first port with the third port when the first push button is pressed, the second valve plug being devised to place in fluid communication he second port with the third port when the second push button is pressed, both of the first and second push buttons projecting outwardly of the handle so as to be easily accessible and operable with a finger when the handle is held in one hand, (ii) a fluid irrigation tube having one end connected to and in fluid communication with the one port of the valve and another end extending outside the handle and connectable to the source of flushing liquid;

(iii) a fluid irrigation tube having one end connected to and in fluid communication with the one port of the valve and another end extending outside the handle and connectable to the source of flushing liquid;

(iii) a fluid evacuation tube having one end connected to and in fluid communication with the second port of the valve and another end extending outside the handle and connectable to the source of vacuum;

(iv) a fluid connection tube having one end connected to and in fluid communication with the third port of the valve and another end connected to a fluid opening provided in the cylinder between the front and rear ends thereof.

Advantageously, the suction and irrigation cartridge (B) may further include:

(v) a shaft-receiving sleeve sized and shaped to act as an internal lining within said cylinder, said sleeve having a lateral opening acting as said fluid opening provided in said cylinder and to which the fluid connection tube is connected.

Moreover, the valve (i), fluid tubes (ii), (iii) and (iv) and sleeve (v) of the section and irrigation cartridge (B) can be made and connected to each other so as to form a unitary, disposable structure removably insertable within the pistol-shaped holder (A) when both parts thereof are detached.

The interchangeable surgical tool (C) used in accordance with the invention includes:

(i) a cylindrical shaft sized in diameter and length to fit into the cylinder, the shaft having front and rear ends and including:

an annular groove positioned to be in front of and in fluid communication with the fluid opening when the shaft is fully inserted into the cylinder through the open front end thereof;

an internal bore opening into the annular groove and extending therefrom up to the front end of the shaft; and sealing means located forwardly and rearwardly of the annular groove to prevent flushing liquid from leaking out of the cylinder when the shaft is inserted therein and liquid is allowed to flow through the annular groove and bore; and (ii) a trocar in the form of a long, rigid tube connected to and projecting sustantially coaxially away from the front end of the shaft, this trocar having an open free end distant from the shaft and an internal passage extending between the open free end and the internal bore of the shaft, the passage placing the open free end and the internal bore in fluid communication.

The surgical tool (C) may further include:

(iv) bipolar electrodes affixed to the free end of the trocar (ii) so as to be close to each other; and (v) insulated electric conductors extending within the surgical tool (C) from the free end of the trocar to the rear end of the shaft, these conductors having front ends electrically connected to the electrodes, respectively, and rear ends that project away from the rear end of the shaft through the rear end of the hollow cylinder which is open for this purpose.

By proper electrical connection of these conductors to an external electrosurgical generator, the surgical instrument thus becomes useful for electrocautery.

The surgical tool (C) may further include:

(vi) at least one optic fiber extending within the surgical tool (C) along at least the trocar, thus at least one fiber having one end adjacent the free end of the trocar and another end extending externally of said tool at the rear end of the shaft through the rear end of the hollow cylinder.

Once again, by proper connection of the other end of the at least one optic fiber to a bisualization apparatus or a laser light source, the surgical instrument thus becomes useful for laparoscopy or laser surgery.

The invention and its advantages will become much more apparent from the following non-restrictive description of a preferred embodiment thereof, given with reference to the accompanying drawings.

BRIEF DESCRIPTION OF THE DRAWINGS

FIG. 2 is a side elevational, cross-section view of the instrument shown in FIG. 1, in assembled from;

FIG. 3 is a side elevational, cross-section view of a surgical tool for use with the instrument shown in FIG. 1 to carry out electrocautery; and FIG. 4 is a side elevational, cross-section view of a surgical tool for use with the instrument shown in FIG. 3 to carry out laser surgery.

DESCRIPTION OF A PREFERRED EMBODIMENT

The multi-functional surgical instrument 1 according to the invention for use in carrying out laparoscopic surgery as shown in the accompanying drawings, comprises in combination: a pistol-shaped holder 10, a suction and irrigation cartridge 20, and an interchangeable surgical tool 40, each of which will be described in greater details hereinafter.

Figure 1:
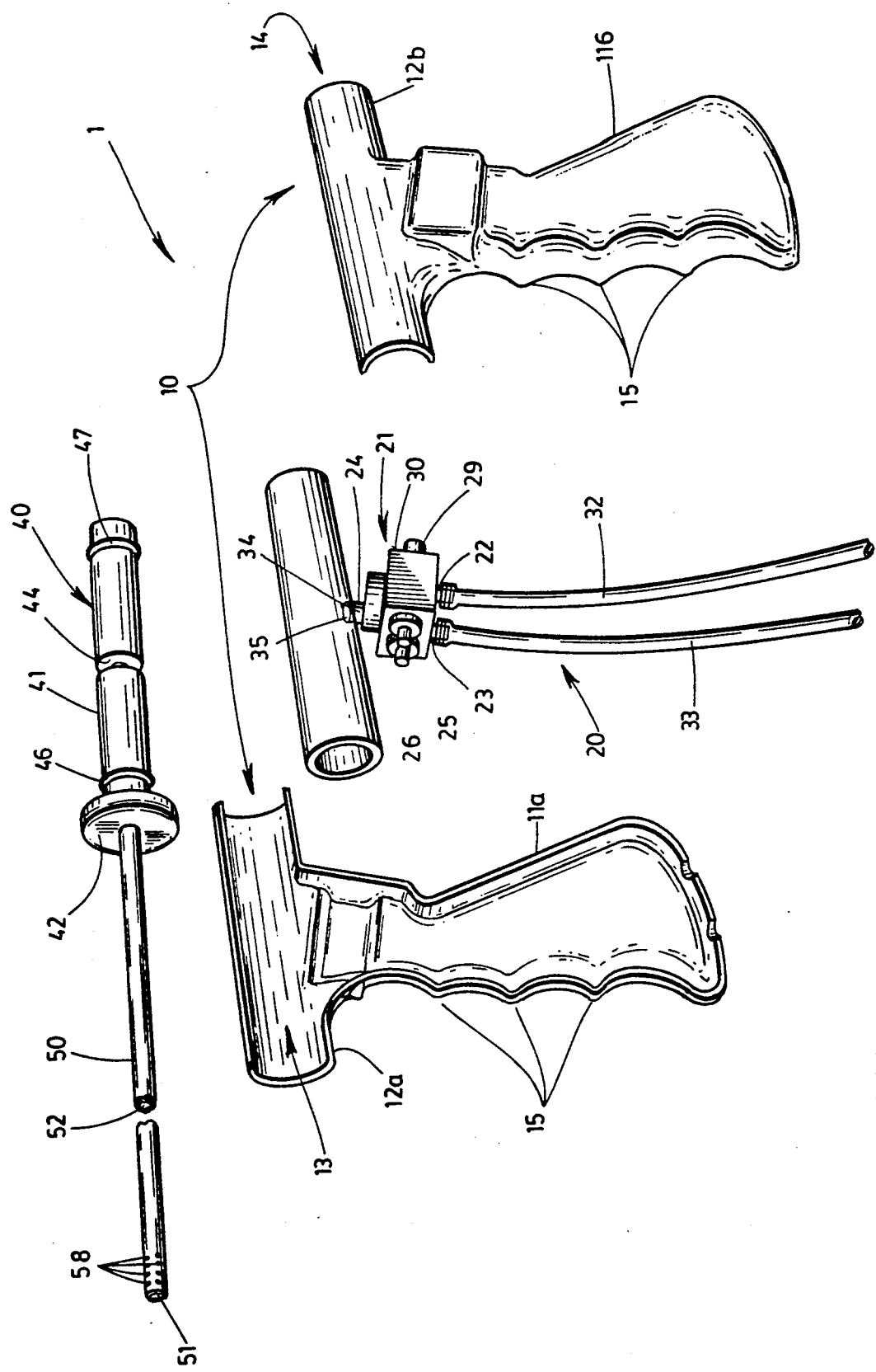
FIG. 1 is an exploded perspective view of a multifunctional surgical instrument according to a preferred embodiment of the invention.
Figure 2:
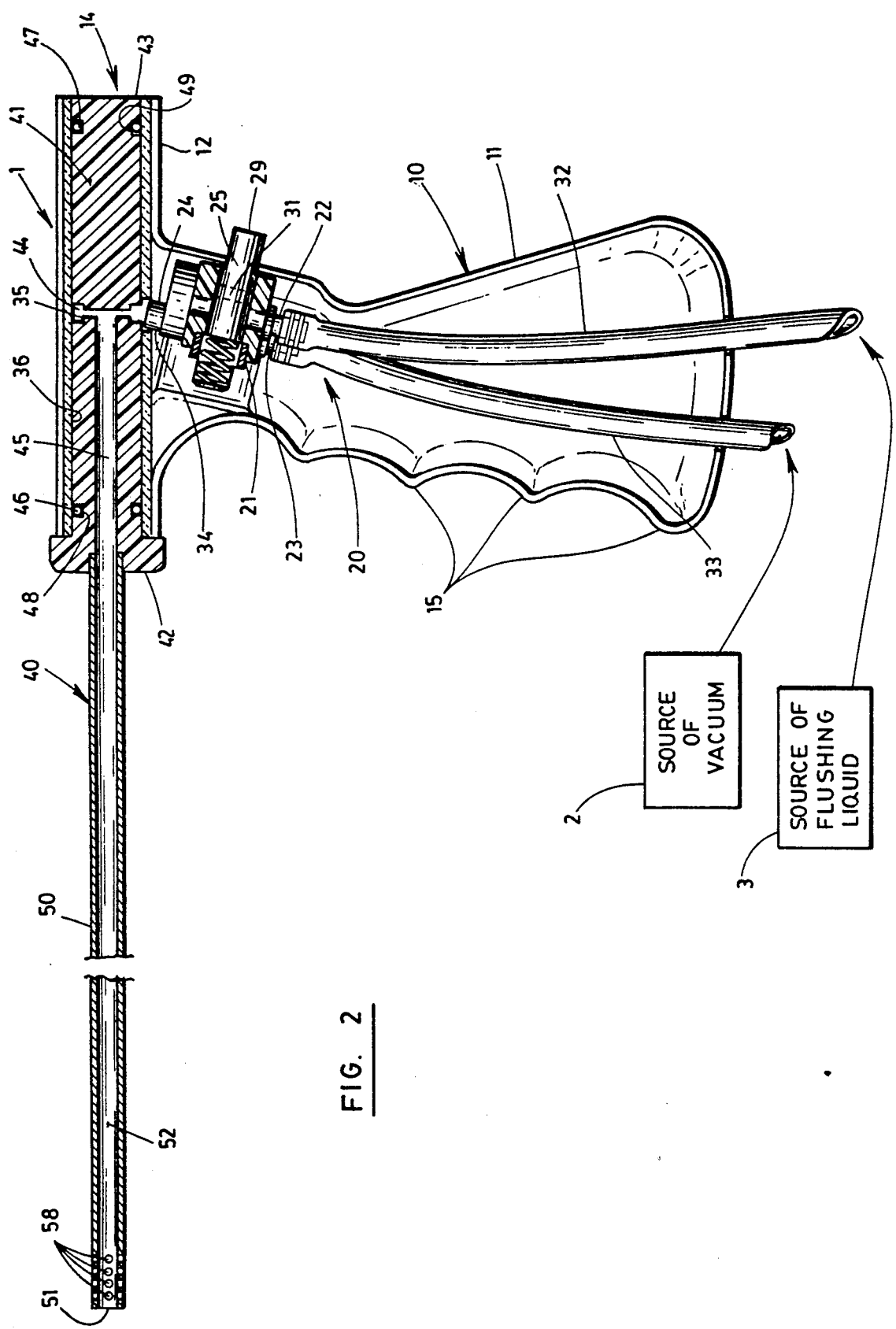

As clearly shown in FIGS. 1 and 2, the pistol-shaped holder 10 includes a hollow handle 11 shaped as a pistol-grip, on top of which integrally extends a hollow cylinder 12 shaped, positioned and oriented as a pistol barrel. As better shown in FIG. 1, the pistol-shaped holder 10 is preferably made of two symmetrical parts preferably molded from plastic material, that are detachably connected either by a screw (not shown) or by snapping and each defines half of the handle 11a or 11b, and half of the cylinder 12a or 12b. The cylinder 12 has an open front end 13 and a rear end 14 which is also preferably open. The handle which is designed to be held with one hand only is preferably formed with corrugations 15 to give a better hand-grip.

The handle 11 is sized and shaped to receive and hold the suction and irrigation cartridge 20 whose purpose is to make the instrument 1 operatively connectable to a source of vacuum 2 of say, about −500 Hg, and/or a source of flushing liquid 3.

As shown in FIGS. 1 and 2, the cartridge 20 includes a three way valve 21 mounted in a cavity 16 especially provided for this purpose inside the handle 11. The valve 21 comprises a plastic body including three ports 22, 23 and 24 and a pair of spring-biased valve plugs 25, 26 slidably mounted in a pair of parallel channels 27, 28, and operable by a pair of corresponding push-buttons 29, 30, respectively.

One of the valve plugs, say 25, has an inner passage 31 and is devised to place in fluid communication the first port 22 with the third port 24 when the first push button 29 is pressed. The other valve plug 26 also has an inner passage and is devised to place in fluid communication the second port 23 with the third port 24 when the second push button 30 is pressed.

As clearly shown in FIG. 2, both push buttons 29, 30 are positioned to project outwardly of the handle 11 through an opening provided for this purpose, so as to be easily accessible and operable with a finger, preferably the thumb, when the handle is held in one hand.

The cartridge 20 also includes a set of tubes including:

a fluid irrigation tube 32 that is made of plastic material and has one end connected to and in fluid communication with the one port 22 of the valve 21 and another end extending outside the handle 11 and detachably connectable in a manner known per se to the source of flushing liquid 3;

a fluid evacuation tube 33 having one end connected to and in fluid communication with the second port 23 of the valve 21 and another end extending outside the handle and detachably connectable in a manner known per se to the source of vacuum 2; and a fluid connection tube 34 that is also made of plastic material and has one end connected to and in fluid communication with the this port 24 of the valve 21 and another end connected to a lateral opening 35 provided in an optional plastic made, shaft-receiving sleeve 36 sized and shaped to act as an internal lining within the cylinder 12, the lateral opening 35 being positioned at mid-distance between the front and rear ends of the sleeve 36 and acting as a fluid opening provided in the cylinder 12.

Advantageously, the valve 21, the fluid tubes 32, 33 and 34 and sleeve 36 of the suction and irrigation cartridge 20 are made and connected to each other so as to form a unitary, disposable structure removably insertable within the pistol-shaped holder 10 when both parts thereof are detached.

The third and last component of the surgical instrument 1 according to the invention, i.e. the interchangeable surgical tool 40, includes a cylindrical shaft 41 sized in diameter and length to fit into the sleeve 36 or directly into the cylinder 12 when there is no sleeve. The shaft 51 has front and rear ends 42, 43 respectively and includes an annular groove 44 positioned to be in front of and in fluid communication with the lateral opening 35 of the sleeve 36 or with the corresponding fluid opening of the cylinder when there is no sleeve and the shaft is fully inserted into the cylinder 12 through the open front end 13 thereof.

The shaft 41 also includes an internal bore 45 (see FIG. 2) opening into the annular groove and extending therefrom up to the front end 42 of the shaft.

The shaft further includes sealing means located forwardly and rearwardly of the annular groove 44 to prevent the flushing liquid from leaking out of the cylinder or sleeve when the shaft 41 is inserted therein and liquid is allowed to flow throuh the annular groves 44 and bore 45.

The sealing means of the cylindrical shaft 41 preferably consists of a pair of O-rings 46, 47 mounted in small grooves 48, 49 made in the shaft, the small grooves extending parallel to the annular groove 44 opposite distances from this annular groove along the shaft.

As is clearly shown in FIGS. 1 and 2, the front end 42 of the shaft 41 is preferably shaped to form a stop member to limit insertion of the shaft 41 into the sleeve 36 and ensure after such an insertion that the annular groove 44 of this shaft extends just in front of the lateral opening 35 of the sleeve 36 or the corresponding opening made in the cylinder 12 when no sleeve is used.

When, as indicated hereinabove, the opening 35 is made at mid-length of the sleeve 36 and this sleeve is equal in length to the cylinder 12, one can see that the shaft may be inserted in any direction, that is through any ends 13, 14 of the cylinder 12, depending on what is more convenient for the surgeon who holds the handle 11.

In addition to the shaft, the surgical tool 40 also includes a trocar 50 in the form of a long, rigid tube rigidly connected to and projecting substantially coaxially away from the front end 42 of the shaft 41. The trocar 50 which may be up to 5 mm wide, is intended to be inserted in the 1 cm cannula to perform or complete surgery. It is electrically insulated and has an open free end 51 distant from the shaft 41, and an internal passage 52 extending between the open free end 51 and the internal bore 45 of the shaft to place the same in fluid communication.

As can now be better understood, the surgical instrument 1 combining the above structural elements is very simple yet efficient in structure and can be used in a very effcient way in laparoscopic surgery for suction of physiological matter or irrigation purpose. It may also be used for evacuating by suction stones or blood clots from the internal cavity where surgery is being made. To avoid that a stone or blood clot inadvertently blocks the open free end 51 of the trocar 50 and makes it inoperative for suction or irrigation purpose, lateral holes 58 may be provided on the trocar adjacent its free end.

In all cases, it will be appreciated that release of any push-buttons 29, 30 pressed with a finger immediately stops the suction or irrigation that is being done.

Thanks to its pistol-grip handle 11 incorporating the valve-actuating push buttons 29, 30, it is very handy and easy to use. Moreover, thanks to the way the surgical tool 40 and cartridge 20 are designed and mounted, it is rather fast and easy to interchange any one or both of them whenever required. Indeed, the shaft 41 of the tool 40 has merely to be inserted and pushed down inside the sleeve 36 and/or cylinder 12 until the stop bears onto the open end 13 or 14 to have the fluid and vacuum connection made and effective. Moreover, one has only to open the holder, remove the cartridge assembly and insert a new one to make the instrument immediately reusable.

FIG. 3 shows another surgical tool 40' that can be used in place of the tool 40 previously described to add another function to the instrument 1 whenever desired. In this FIG. 3, all the elements similar to those already described with reference to FIGS. 1 and 2 have been identified with the same reference numerals, with a distinguishing prime (').

The only difference between tool 40' and tool 40 is that the former further includes bipolar electrodes 53, 54 affixed to the free end 51' of the trocar 50' so as to be close to each other and a pair of insulated electric conductors 55, 56 extending within the surgical tool 40' from the free end of the trocar 50 to the rear end 43' of the shaft 41', these conductors having front ends electrically connected to the electrodes 53, 54 respectively, and rear ends that project away from the rear end 43' of the shaft 41' through the rear end of the hollow cylinder or sleeve and are electrically connectable to an external electrosurgical generator 4.

This tool 40' makes the surgical instrument 1 useful for electrocautery.

FIG. 4 shows a further surgical tool 40" that can be used in place of the tool 40 or 40', to add a further function to the instrument 1. Once again, the elements is similar to those already described with reference to FIGS. 1 and 2, have been identified with the same reference numerals, with a distinguishing second (").

The only difference between tool 40" and tool 40 is that the former includes at least one and preferably a bundle of optic fibers 57 extending within it along at least the trocar 50" and preferably along both the trocar and shaft 41", the optic fiber 57 or bundle of optic fibers having one end adjacent the free end 51" of the trocar 50" and another end extending externally of the tool 40 close to the holder.

By proper connection of the other end of the optic fiber 57 or bundle of optic fibers to a visualization apparatus 5 or a laser light source 6 in a manner known per se the surgical instrument becomes useful for laparoscopy or laser surgery.

It may be noticed and appreciated that the conductors 55, 56 or optic fiber(s) 57 occupy only part of the passage 52' or 52" and thus make the tool 40' or 40" still useful for suction or irrigation purposes. In practice however, when the tool 40' is used for electrocautery, one should not irrigate while the current is switched on, since this would substantially reduce the efficiency of the electrocautery in addition to causing short circuit.

It may also be noticed and appreciated that the conductors 55, 56 and optic fiber(s) 57 could easily be incorporated into a single tool, thereby making it fully versatile and useful for suction and irrigation purposes, electrocautery, laparoscopy and laser surgery.

In summary, the surgical instrument 1 according to the invention as disclosed hereinabove is particularly well designed for use in laparoscopic surgery.

It incorporates a trocar which is sized for insertion into the conventional cannulas used in laparoscopy.

The instrument allows physiological liquid, blood clots, stones and other solid to be removed from the cavity subject to surgery. It also allows irrigation of the internal cavity. The fluid jet may even be adjusted to allow sweeping of the organic walls.

The surgical instrument according to the invention is waterproof and non-conductive. It may incorporate optic fibers making it useful as a laser that can be activated together with the suction and irrigation.

It may also incorporate electrodes connectable to an electrosurgical generator that can be switched on to perform electrocautery simultaneously with suction.

It can be easily sterilized with a sterilizing gas or with gamma rays.

The suction and irrigation cartridges in the handle may be made disposable, thereby avoiding contamination by inefficient cleaning of the internal mechanism of the valve and/ dead spaces in which could store biogical substances.

Accordingly, the surgical instrument according to the invention is simple yet efficient, easy-to-use and multifunctional.

What is claimed is:

1. A multi-functional surgical instrument for use in carrying out laparoscopic surgery, said instrument comprising:
A) a pistol-shaped holder, said holder including:
   (i) a handle shaped as a pistol-grip; and
   (ii) a hollow cylinder shaped, positioned and oriented as a pistol barrel on top of the handle; said cylinder having an open front end and a rear end,
B) a suction and irrigation cartridge mounted within said handle and connectable to a source of vacuum and a source of flushing liquid, respectively, said cartridge including:
   (i) a three way valve mounted inside said handle, said valve including:
      first, second and third fluid ports and
      first and second spring-biased valve plugs operable by first and second push-buttons respectively,
      said first valve plug being devised to place in fluid communication said first port with said third port when said first push button is pressed,
      said second valve plug being devised to place in fluid communication said second port with said third port when said second push button is pressed,
      both of said first and second push buttons projecting outwardly of said handle so as to be easily accessible and operable with a finger when said handle is held in one hand,
   (ii) a fluid irrigation tube having one end connected to and in fluid communication with the one port of the valve and another end extending outside said handle and connectable to said source of flushing liquid;
   (iii) a fluid evacuation tube having one end connected to and in fluid communication with the second port of the valve and another end extending outside said handle and connectable to said source of vacuum;
   (iv) a fluid connection tube having one end connected to and in fluid communication with the third port of the valve and another end connected to a fluid opening provided in said cylinder between the front and rear ends thereof; and
C) an interchangeable surgical tool including:
   (i) a cylindrical shaft sized in diameter and length to fit into said cylinder, said shaft having front and rear ends and including:
      an annular groove positioned to be in front of and in fluid communication with said fluid opening when said shaft is fully inserted into said cylinder through the open front end thereof;
      an internal bore opening into said annular groove and extending therefrom up to the front end of the shaft; and sealing means located forwardly and rearwardly of the annular groove to prevent flushing liquid from leaking out of the cylinder when the shaft is inserted therein and liquid is allowed to flow through the annular groove and bore; and (ii) a trocar in the form of a long, rigid tube connected to and projecting substantially coaxially away from the front end of the shaft, said trocar having an open free end distant from said shaft and an internal passage extending between said open free end and the internal bore of the shaft, said passage placing said open free end and said internal bore in fluid communication.

2. The surgical instrument of claim 1 wherein the suction and irrigation cartridge (B) further includes:

(v) a shaft-receiving sleeve sized and shaped to act as an internal lining within said cylinder, said sleeve having a lateral opening acting as said fluid opening provided in said cylinder and to which the fluid connection tube is connected.

3. The surgical instrument of claim 2, wherein:

the pistol-shaped holder (A) is made of two symmetrical parts that are detachably connected and each define half of the handle (i) and half of the cylinder (ii); and the valve (i), fluid tubes (ii), (iii) and (iv) and sleeve (v) of the section and irrigation cartridge (B) are made and connected to each other so as to form a unitary, disposable structure removably insertable within said pistol-shaped holder (A) when both parts thereof are detached.

4. The surgical instrument of claim 3, wherein the surgical tool (C) further includes:

(iii) a stop member adjacent the front end of the shaft to limit insertion thereof into the sleeve and ensure after such an insertion that the annular groove of said shaft extends just in front of the lateral opening of the sleeve (v) of the cartridge (B).

5. The surgical instrument of claim 4 wherein the sealing means of the cylindrical shaft consists of a pair of O-rings mounted in small grooves made in said shaft, said small grooves extending parallel to the annular groove at opposite distances from said groove along said shaft.

6. The surgical instrument of claim 5, wherein the rear end of the hollow cylinder is open and the surgical tool (C) further includes:

(iv) bipolar electrodes affixed to the free end of the trocar (ii) so as to be close to each other; and (v) insulated electric conductors extending within said surgical tool (C) from the free end of the trocar to the rear end of the shaft, said conductors having front ends electrically connected to said electrodes, respectively, and rear ends that project away from the rear end of the shaft through the rear end of the hollow cylinder and are electrically connectable to an external electrosurgical generator, whereby said surgical instrument is useful for electrocautery.

7. The surgical instrument of claim 5, wherein the surgical tool (C) further includes:

(vi) at least one optic fiber extending within said surgical tool (C) along at least said trocar, said at least one fiber having one end adjacent the free end of said trocar and another end extending externally of said tool close to said the holder (A)

whereby, by proper connection of the other end of said at least one optic fiber to a visualization apparatus or a laser light source, said surgical instrument is useful for laparoscopy or laser surgery.

8. The surgical instrument of claim 5, wherein the surgical tool (C) further includes:

(vi) at least one optic fiber extending within said surgical tool (C) along at least said trocar, said at least one fiber having one end adjacent the free end of said trocar and another end extending externally of said tool at the rear end of the shaft through the rear end of the hollow cylinder, whereby, by proper connection of the other end of said at least one optic fiber to a visualization apparatus or a laser light source said surgical instrument is useful for laparoscopy or laser surgery.

9. The surgical instrument of claim 1, wherein the surgical tool (C) further includes:

(iii) a stop member adjacent the front end of the shaft to limit insertion thereof into the sleeve and ensure after such an insertion that the annular groove of said shaft extends just in front of the fluid opening provided in said cylinder.

10. The surgical instrument of claim 9, wherein the sealing means of the cylindrical shaft consists of a pair of O-rings mounted in small grooves made in said shaft, said small grooves extending parallel to the annular groove at opposite distances from said groove along said shaft.

11. The surgical instrument of claim 9, wherein the rear end of the hollow cylinder is open and the surgical tool (C) further includes:

(iv) bipolar electrodes affixed to the free end of the trocar (ii) so as to be close to each other; and (v) insulated electric conductors extending within said surgical tool (C) from the free end of the trocar to the rear end of the shaft, said conductors having front ends electrically connected to said electrodes, respectively, and rear ends that project away from the rear end of the shaft through the rear end of the hollow cylinder and are electrically connectable to an external electrosurgical generator, whereby said surgical instrument is useful for electrocautery.

12. The surgical instrument of claim 11 wherein the surgical tool (C) further includes:

(vi) at least one optic fiber extending within said surgical tool (C) along at least said trocar, said at least one fiber having one end adjacent the free end of said trocar and another end extending extenally of said tool at the rear end of the shaft through the rear end of the hollow cylinder, whereby, by proper connection of the other end of said at least one optic fiber to a visualization apparatus or a laser light source said surgical instrument is useful for laparoscopy or laser surgery.

13. The surgical instrument of claim 9, wherein the surgical tool (C) further includes:

(vi) at least one optic fiber extending within said surgical tool (C) along at least said trocar, said at least one fiber having one end adjacent the free end of said trocar and another end extending extenally of said tool close to said the holder (A)

whereby, by proper connection of the other end of said at least one optic fiber to a visualization apparatus or a laser light source said surgical instrument is useful for laparoscopy or laser surgery.

* * * * *